United States Patent
Schmitz

(10) Patent No.: US 6,786,895 B1
(45) Date of Patent: Sep. 7, 2004

(54) DISPOSABLE ABSORBENT ARTICLE HAVING BARRIER MEANS, AND METHOD OF ITS MANUFACTURE

(75) Inventor: Christoph Johann Schmitz, Euskirchen-Stotzheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 103 days.

(21) Appl. No.: 10/019,036

(22) PCT Filed: Jun. 26, 2000

(86) PCT No.: PCT/US00/17528
§ 371 (c)(1),
(2), (4) Date: Dec. 20, 2001

(87) PCT Pub. No.: WO01/01907
PCT Pub. Date: Jan. 11, 2001

(30) Foreign Application Priority Data

Jul. 2, 1999 (EP) .............................................. 99112653

(51) Int. Cl.⁷ ............................ A61F 13/15; A61F 13/20
(52) U.S. Cl. ......................... 604/385.28; 604/385.101; 604/385.19
(58) Field of Search ..................... 604/385.01, 385.08, 604/385.101, 385.19, 385.22, 385.24–385.3, 393–399

(56) References Cited

U.S. PATENT DOCUMENTS

| | | | |
|---|---|---|---|
| 4,662,877 A | | 5/1987 | Williams |
| 4,743,246 A | | 5/1988 | Lawson |
| 5,304,160 A | * | 4/1994 | Igaue et al. ............. 604/385.28 |
| 5,527,302 A | * | 6/1996 | Endres et al. .......... 604/385.21 |
| 5,569,227 A | * | 10/1996 | Vandemoortele et al. ... 604/382 |
| 5,653,703 A | | 8/1997 | Roe et al. ............... 604/385.01 |
| 5,662,637 A | * | 9/1997 | Kitaoka et al. ........ 604/385.28 |
| 5,817,086 A | * | 10/1998 | Kling .................... 604/385.19 |
| 6,120,632 A | | 9/2000 | Dragoo et al. ............... 156/164 |
| 6,494,872 B1 | * | 12/2002 | Suzuki et al. .......... 604/385.26 |

FOREIGN PATENT DOCUMENTS

| | | | | |
|---|---|---|---|---|
| EP | 376022 A2 | | 7/1990 | |
| EP | 0 357 298 | | 11/1994 | |
| EP | 631767 A1 | * | 1/1995 | ........... A61F/13/15 |
| EP | 0 908 162 | | 4/1999 | |
| EP | 0 955 028 | | 11/1999 | |
| EP | 1064899 A1 | * | 1/2001 | ........... A61F/13/15 |
| EP | 0 486 006 | | 8/2001 | |
| GB | 2 328 158 | | 2/1999 | |
| JP | 0542181 A | * | 2/1993 | |
| JP | 8-196565 A | | 6/1996 | |
| JP | 8322878 A | * | 10/1996 | |
| WO | WO 97/39710 | | 10/1997 | |
| WO | WO 9814154 A1 | | 4/1998 | ........... A61F/13/15 |
| WO | WO9963921 A1 | * | 12/1999 | |
| WO | WO0101907 A1 | * | 1/2001 | |

OTHER PUBLICATIONS

Translation of JP 5–42181.*

* cited by examiner

Primary Examiner—Karin Reichle
(74) Attorney, Agent, or Firm—Jay A. Krebs; Ken K. Patel; Steven W. Miller

(57) ABSTRACT

A disposable absorbent article, and a method of manufacture of the disposable absorbent article, which better contains fecal material within the article, and which prevents leakage of fecal material out of the article, and/or prevents movement of fecal material from the anal region to the genital region is described herein. The absorbent article utilizes barrier cuffs, an absorbent core, and a topsheet with at least one cut in the intermediate region of the absorbent article such that part of the intermediate region of the topsheet is lifted out of the plane of the rest of the topsheet by the barrier cuffs. The lifted portion forms a transverse barrier and a pocket between the topsheet and the absorbent core.

9 Claims, 3 Drawing Sheets

DISPOSABLE ABSORBENT ARTICLE HAVING BARRIER MEANS, AND METHOD OF ITS MANUFACTURE

The present invention relates to absorbent articles such as disposable diapers, and more particularly to absorbent articles having barrier means for the containment of fecal matter. The invention also relates to methods of manufacture of the absorbent articles having barrier means for the containment of fecal matter.

The major function of absorbent articles such as disposable diapers and incontinence briefs or undergarments is to absorb and contain body exudates. Such articles are thus intended to prevent body exudates from soiling, wetting, or otherwise contaminating clothing or other articles, such as bedding, that come into contact with the wearer. The most common mode of failure for such products occurs when body exudates leak out of the gaps between the article and the wearer's leg or waist. Fecal material that is not absorbed by the absorbent article can work its way past the gaps in the article in the legs or waist of the wearer.

Contemporary disposable diapers have a front waist region, a rear waist region and an intermediate region between the front and rear waist regions; these regions being located within a front waist edge, a rear waist edge, and two longitudinal edges. Contemporary diapers comprise a liquid pervious topsheet, a liquid-impervious backsheet, and an absorbent core positioned between the topsheet and the backsheet.

Disposable diapers may also be provided with barrier cuffs which inhibit fecal material or gushes of urine or liquids from soiling the wearer's clothing The barrier cuffs restrain the free flow of this material to hold such material within the diaper. U.S. Pat. No. 4,743,246, issued on May $10^{th}$ 1988, discloses an absorbent article having barrier cuffs.

Various prior art patent applications have disclosed a cut-out hole in the top sheet to provide a means for fecal material to be held within the disposable diaper, behind the topsheet and out of contact with the wearer's skin. In some of these patent applications an elastic strip is used to apply tension to a region around the cut-out hole in order to maintain an open aperture. Usually the elastic strips are attached directly to the topsheet, usually to the side of the topsheet which faces away from the body of the wearer. For example U.S. Pat. No. 4,662,877, published on May $5^{th}$ 1987 discloses a topsheet with an aperture in the central crotch region of the diaper with zones of elastication in the topsheet tending to apply tensioning forces to the topsheet for urging it away from the underlying absorbent core. EP-A-0 357 298, published on $7^{th}$ Mar. 1990; EP-A-0 486 006, published on $20^{th}$ May 1992; and GB-A-2 328 158, published on $17^{th}$ Feb. 1999, also teach various means of applying elastic tensioning forces to the topsheet in order to maintain an open aperture.

It is an object of the present invention to provide a disposable absorbent article, and a method of manufacture of the disposable absorbent article, which better contains fecal material within the article, and which prevents leakage of fecal material out of the article, and/or prevents movement of fecal material from the anal region to the genital region. The absorbent article comprises a barrier cuff adjacent to the longitudinal edges of the disposable absorbent article, each barrier cuff having a proximal edge and a distal edge; and spacing means associated with each barrier cuff distal edge so that the distal edge is spaced away from the top surface of the topsheet.

SUMMARY OF THE INVENTION

The object of the present invention is achieved by means of a top sheet comprising at least one cut in the intermediate region, each cut extending from a first cut end to a second cut end between barrier cuffs, wherein the topsheet adjacent to each of the cut ends is attached to the barrier cuff between the proximal edge and the distal edge, so that a part of the intermediate region of the topsheet is lifted out of the plane of the rest of the topsheet by means of the barrier cuffs to form at least one transverse barrier and a pocket between the topsheet and the absorbent core.

DETAILED DESCRIPTION OF THE INVENTION

As used herein, the term "disposable absorbent article" refers to articles which absorb and contain body exudates and more specifically refers to articles which are placed against or in proximity to the body of the wearer to absorb and contain the various exudates discharged from the body, and which are intended to be discarded after a single use (i.e. they are not intended to be laundered or otherwise restored or reused). The term refers to sanitary products including catamenial products, but in particular the term refers to diapers and adult incontinent pants. As used herein the term "diaper" refers to a garment generally worn by infants and incontinent persons that is worn about the lower torso of the wearer, and this term is used to exemplify most preferred disposable absorbent articles. Whilst the term "diaper" is used to exemplify the invention, it is not intended to be limiting.

Figure 1:
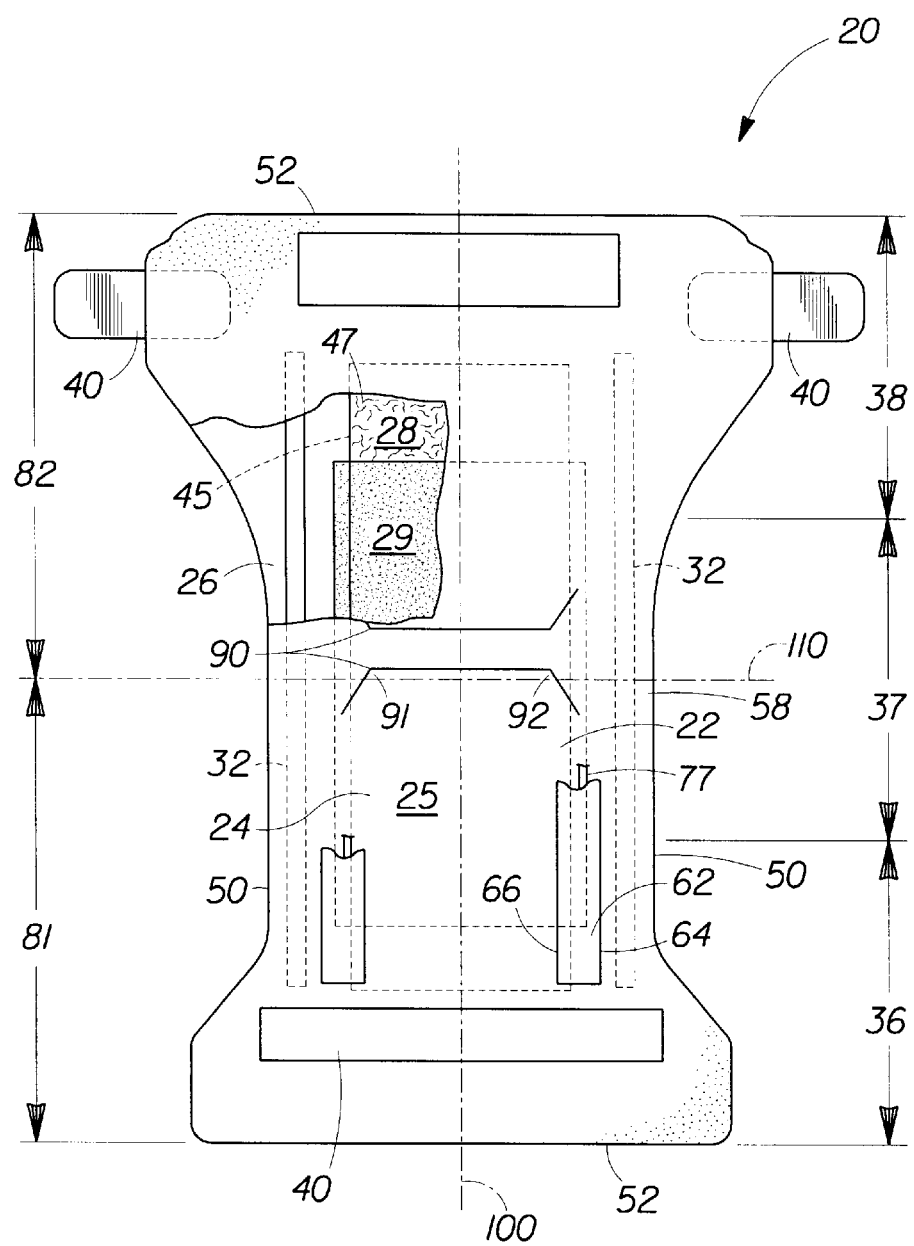
FIG. 1 is a plan view of a disposable absorbent article in a flat-out state, with a cutaway view, made according to the present invention.
Figure 2:
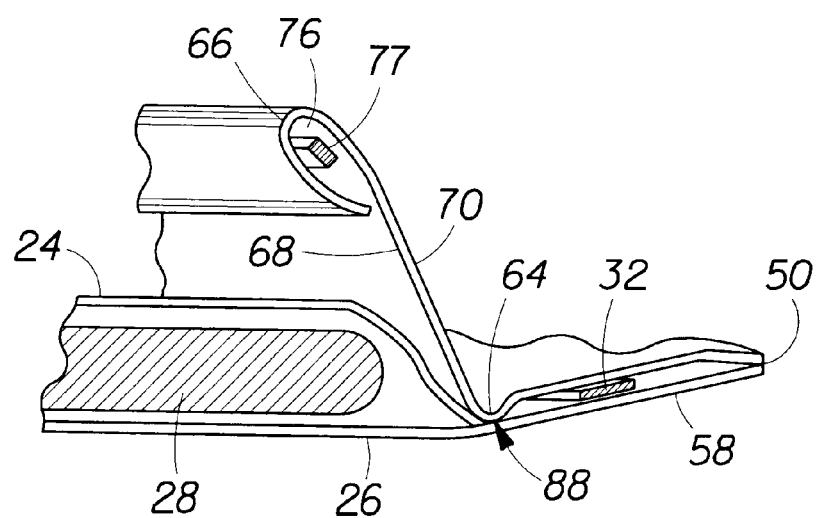
FIG. 2 is a cross-section of a barrier cuff suitable for use in the absorbent article shown in FIG. 1.

A diaper 20 according to the invention is shown in FIG. 1 in a flat-out state, with portions of the structure being cut-away to more clearly show the construction of the diaper 20. The portion of the diaper 20 which faces the wearer is oriented towards the viewer. As shown in FIG. 1, the diaper comprises a liquid pervious topsheet 24, the top surface of the topsheet 24 being designated 25; a liquid impervious backsheet 26; an absorbent core 28, which is preferably positioned between at least a portion of the topsheet 24 and the backsheet 26; a fastening system generally designated 40; gasketing cuffs each comprising a side flap 58 and flap elastic members 32. The diaper further comprises barrier cuffs 62 each having a proximal edge 64, a distal edge 66, and spacing means 76 (shown in FIG. 2) such as a spacing elastic member 77 for spacing the distal edge 66 away from the topsheet top surface 25. The barrier cuffs 62 further comprise, as shown in FIG. 2, an inboard surface 68 and an outboard surface 70. The diaper may further comprise a liquid handling structure 29 which is preferably positioned between the topsheet 24 and the absorbent core 28.

The diaper 20 is shown in FIG. 1 to have a front waist region 36, a rear waist region 38 opposed to the front waist region 36 and an intermediate region 37 located between the front waist region and the rear waist region. The diaper 20 further has a first region 81 juxtaposed with the front of the wearer while the diaper 20 is being worn and a second region 82 opposed to the first region 81 and juxtaposed with the back of the wearer while the diaper 20 is being worn. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the transverse centerline 110 of the diaper 20. In FIG. 1 the first region 81 is shown as extending from one end edge 52 to the transverse centerline 110 and the second region 82 is shown as extending from the opposing end edge 52 to the transverse centerline 110. For purposes of discussion, the transverse centerline 110 is shown as the boundary between the first region 81 and the second region 82 in FIG. 1. However, the boundary between the first region 81 and the second region 82 may be positioned at other locations, for example closer to one of the respective end edges 52. The first region 81 being juxtaposed with the front of the wearer should be superior in the handling of urine. The second region being juxtaposed with the back of the wearer should be superior in the handling of faecal material, in particular low-viscosity faecal material.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use). For unitary absorbent articles, the chassis 22 comprises the main structure of the diaper with other features added to form the composite diaper structure.

FIG. 1 shows an embodiment of the diaper 20 in which the topsheet 24 and the backsheet 26 have length and width dimensions generally larger than those of the absorbent core 28 and the liquid handling structure 29. The topsheet 24 and the backsheet 26 extend beyond the edges of the absorbent core 28 to thereby form the periphery of the diaper 20.

While the topsheet 24, the backsheet 26, and the chassis 22 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993. Other suitable diaper chassis designs, are disclosed in U.S. Pat. No. 5,569,232 entitled "Absorbent Article With Multiple Zone Structural Elastic-Like Film Web Extensible Waist Feature" which issued to Roe et al. on Oct. 29, 1996; U.S. Pat. No. 5,554,144 entitled "Absorbent Article With Multiple Zone Structural Elastic-Like Film Web Extensible Waist Feature" which issued to Roe et al. on Sep. 10, 1996; U.S. Pat No. 5,554,143 entitled "Absorbent Article With Multiple Zone Structural Elastic-Like Film Web Extensible Waist Feature" which issued to Roe et al. on Sep. 10, 1996; U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,556,394 entitled "Absorbent Article With Multiple Zone Structural Elastic-Like Film Web Extensible Waist Feature" which issued to Roe et al. on Sep. 17, 1996. Each of these references is hereby incorporated by reference herein.

The inner surface of the diaper 20 comprises that portion of the diaper 20 which is adjacent to the wearer's body during use (i.e. the inner surface generally is formed by at least a portion of the topsheet 24 and other components joined to the topsheet 24). The outer surface comprises that portion of the diaper 20 which is positioned away from the wearer's body (i.e., the outer surface generally is formed by at least a portion of the backsheet 26 and other components joined to the backsheet 26) during use.

The barrier cuff 62 is preferably formed by fixing portions of a barrier cuff member to the backsheet 26 or topsheet 24 adjacent the longitudinal edge 50 of the diaper 20 with attachment means 88 such as adhesive or by pressure bonding; a leakage resistant seal being formed by the attachment means 88, the barrier cuff 62 and the backsheet 26 or topsheet 24. The barrier cuff comprises a proximal edge 64 and a distal edge 66. The proximal edge 64 is preferably formed inboard of the elasticised leg cuff 32, preferably between the elasticised leg cuff 32 and the side edge of the absorbent core 28, by adjoining a segment of the barrier cuff to the backsheet 26 or topsheet 24 by edge attachment means such as an adhesive bead so as to form a leakage resistant seal along the proximal edge 64. The distal edge 66 is disposed inboard of the proximal edge 64 and is not secured to any underlying elements of the diaper 20. As shown in FIG. 2, the distal edge 66 can be formed by folding the end of the barrier cuff member back upon itself and securing it to another segment of the barrier cuff member by the distal attachment means to form a tunnel. A spacing means 76 such as a spacing elastic member 77 is enclosed in the tunnel that is formed when the end of the barrier cuff member is folded back upon itself; the spacing elastic member 77 being secured in the barrier cuff by the spacing elastic attachment means. The distal edge 66 is thus spaced away from the top surface 25 of the topsheet by the elastic gathering action of the spacing elastic members 77; a channel thereby being formed by at least the first proximal edge 64, the first distal edge 66 and the inboard surface 68 of the barrier cuff 62.

FIG. 1 shows two cuts 90 extending transversely across the topsheet 24 between barrier cuffs 62 (only part of the barrier cuffs 62 are shown for clarity). In this embodiment the cuts 90 extend beyond the first and second ends by means of oblique cuts extending generally in the direction of the respective end edges 52.

Figure 3:
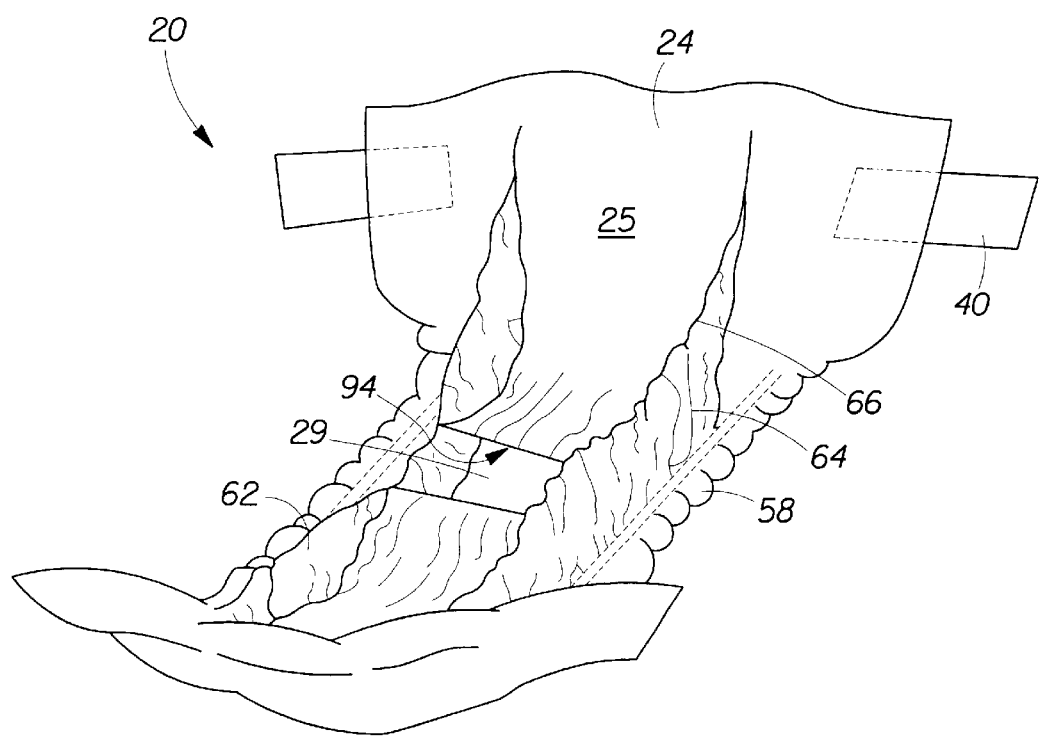
FIG. 3 is a perspective view of a disposable absorbent article of FIG. 1 which is no longer in a flat-out state.
Figure 1:
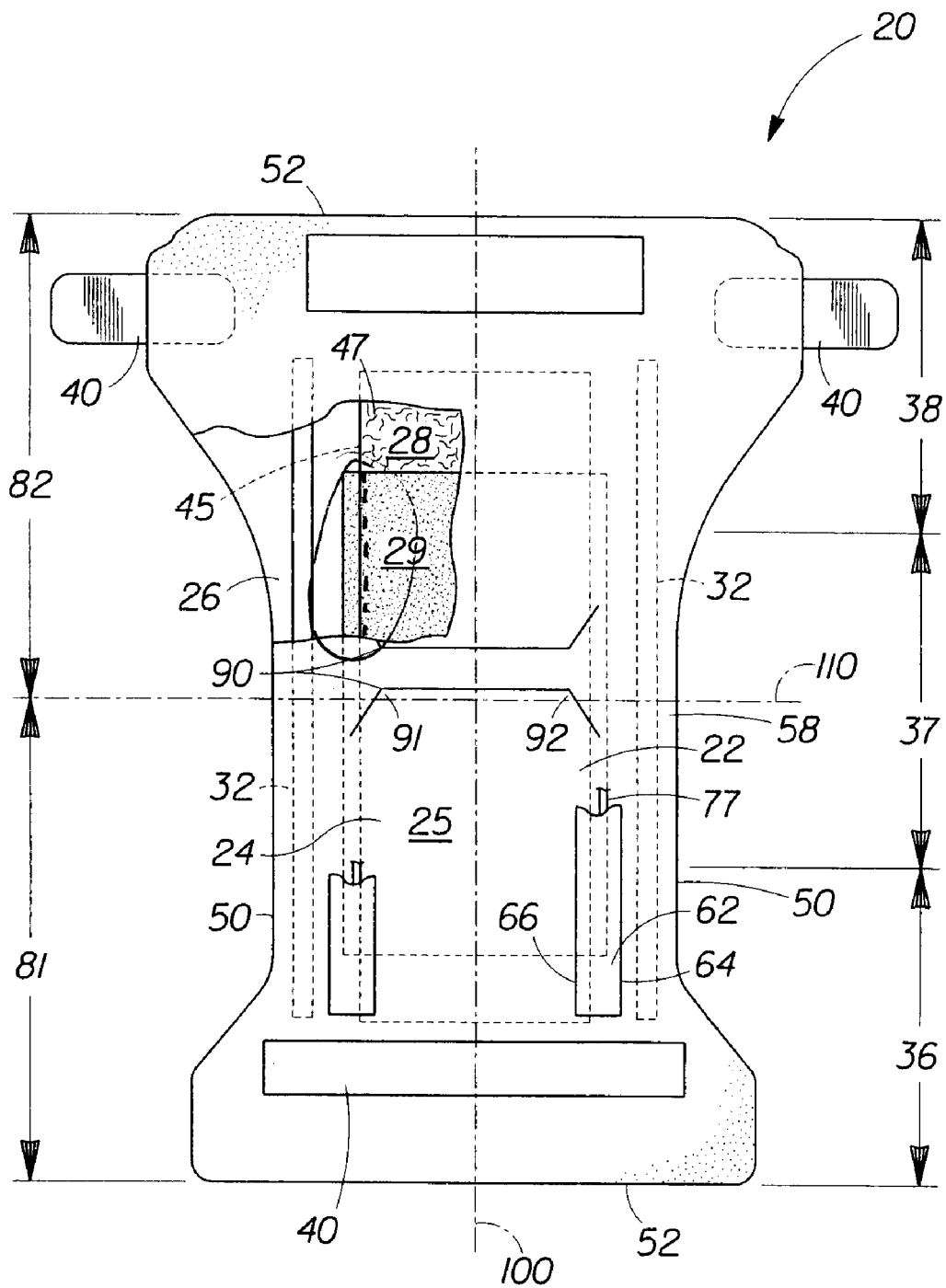

FIG. 3 shows a pocket 94 between the topsheet 24 and a liquid handling component 29, such as an acquisition layer. The pocket 94 is formed by cutting in the transverse direction across the top sheet 24 between the barrier cuffs 62 to form first and second cut ends 91, 92. The first and second cut ends 91, 92 are then attached to the adjacent barrier cuffs 62. In use, the barrier cuffs 62 cause a part of the topsheet 24 which is adjacent to the cut 90 to be lifted out of the plane of the rest of the topsheet 24. This creates a transverse barrier and an adjacent aperture in the top sheet 24 promoting the passage of fecal material through the aperture and into the pocket 94 formed between the topsheet 24 and the acquisition layer 29.

The topsheet comprises at least one cut in the intermediate region, and in preferred embodiments, the topsheet comprises two cuts in the intermediate region. When two cuts are used they are preferably substantially parallel and spaced from 2 mm to 150 mm apart, preferably from 30 mm to 80 mm apart.

In a preferred embodiment of the present invention the first and second cut ends lie at opposite ends of an essentially straight cut oriented transversely across the absorbent article. Alternatively, additional cuts at the first and second cut ends may be used to form at least one U-shaped cut (as shown in FIG. 1), or even at least one H-shaped cut. These additional cuts may be oriented obliquely, or substantially longitudinally. In still another alternative a hole may be cut-out of the topsheet, although preferably no material is cut out of the topsheet in order to avoid waste of material. In still another alternative embodiment the topsheet may be assembled from at least two separate components which are assembled adjacent to each other, or with a gap between them so that the two edges of adjacent topsheet components form the cut or hole.

According to various different embodiments of the present invention the barrier cuffs can, for example, be straight and mutually parallel, straight and mutually non-parallel (i.e. at an angle relative to each other), the barrier cuffs can be either straight or curved; either continuous or intermittent.

The topsheet adjacent to each of the first and second cut ends is attached adjacent to the distal edge of the barrier cuff by any convenient attachment means, for example, by gluing, ultrasonic welding, pressure bonding, thermal bonding (such as hot air seaming).

Preferably, the absorbent article further comprises a means for preventing the absorbent core, or elements of the absorbent core, from passing through the top sheet cut; more preferably the means comprises a liquid handling structure positioned between the topsheet and the absorbent core. Most preferably the web of absorbent material is an acquisition layer.

A pocket is formed between the topsheet and the acquisition layer of the absorbent core. Furthermore, the barrier leg cuff and the top sheet are separate components which are cooperatively attached in order to lift a part of the topsheet out of the plane of the topsheet so as to form the transverse barrier. Additional means may also be used to give the pocket a desired shape, and also to keep the pocket open in order to receive fecal material. For example swelling materials may be disposed along the sides of the pocket which, when wetted, absorb and retain liquid. Suitable swelling materials are absorbent gelling materials. These materials, optionally blended with other materials such as cellulose fluff, may be retained in "bags" which are suitably disposed within, or adjacent to, the pocket. When the swelling materials are wetted, for example by urine, the absorbent gelling materials absorb and retain the liquid making the "bag" more rigid. The rigidity of the "bag" comprising the swelling material contributes to holding the pocket open.

What is claimed is:

1. A disposable absorbent article having a front waist region, a rear waist region and an intermediate region between the front and rear waist regions; the absorbent article comprising a front waist edge, a rear waist edge and two longitudinal edges; the absorbent article comprising a liquid pervious topsheet, a liquid-impervious backsheet, and an absorbent core positioned between the topsheet and the backsheet; the absorbent article further comprising at least two barrier cuffs disposed adjacent to the longitudinal edges of the disposable absorbent article, respectively, each barrier cuff having a proximal edge, a distal edge, an inboard surface and an outboard surface, a spacing means associated with each barrier cuff distal edge so that the distal edge is spaced away from a top surface of the topsheet; wherein the topsheet comprises a cut in the intermediate region, the cut extending from a first cut end to a second cut end between the barrier cuffs; and wherein the topsheet adjacent to each of the cut ends is attached to the inboard surface of adjacent barrier cuff between the proximal edge and the distal edge, so that part of the topsheet in the intermediate region is directly lifted out of a plane containing the rest of the topsheet by means of the barrier cuffs to form a transverse barrier and a pocket between the topsheet and the absorbent core.

2. The disposable absorbent article according to claim 1 further comprising a liquid handling structure positioned between the topsheet and the absorbent core for preventing the absorbent core, or elements of the absorbent core, from passing through the cut in the topsheet.

3. The disposable absorbent article according to claim 2, wherein the liquid handling structure is an acquisition layer.

4. The disposable absorbent article according to claim 1, wherein the spacing means associated with each barrier cuff distal edge comprises at least one spacing elastic member.

5. The disposable absorbent article according to claim 1, wherein the topsheet adjacent to each of the cut ends is attached adjacent to the distal edge of the adjacent barrier cuff.

6. A method of manufacturing a disposable absorbent article having a front waist region, a rear waist region and an intermediate region between the front and rear waist regions; the absorbent article comprising a front waist edge, a rear waist edge, and two longitudinal edges; the absorbent article comprising a liquid pervious topsheet, a liquid-impervious backsheet, and an absorbent core positioned between the topsheet and the backsheet; the absorbent article further comprising at least two barrier cuffs disposed adjacent to the longitudinal edges of the disposable absorbent article, respectively, each barrier cuff having a proximal edge, a distal edge, and an inboard surface and an outboard surface; spacing means associated with each barrier cuff distal edge so that the distal edge is spaced away from a top surface of the topsheet;

wherein the method comprises the steps of:
cutting the topsheet in the intermediate region between the barrier cuffs; and
attaching the topsheet adjacent to each of the cut ends to the inboard surface of the adjacent barrier cuff between the proximal edge and the distal edge, so that a part of the intermediate region of the topsheet is lifted out of a plane containing the rest of the topsheet by means of the barrier cuffs to form a transverse barrier and a pocket between the topsheet and the absorbent core.

7. The method of manufacturing a disposable absorbent article according to claim 6, wherein the topsheet adjacent to each of the cut ends is attached adjacent to the distal edge of the adjacent barrier cuff.

8. The method of manufacturing a disposable absorbent article according to claim 6, wherein the cutting step creates at least one cut substantially in the transverse direction.

9. The method of manufacturing a disposable absorbent article according to claim 6, wherein the topsheet is attached adjacent to each of the cut ends to the distal edge of the adjacent barrier cuff via gluing, ultrasonic welding, or thermal bonding.

* * * * *

UNITED STATES PATENT AND TRADEMARK OFFICE
CERTIFICATE OF CORRECTION

PATENT NO. : 6,786,895 B1
DATED : September 7, 2004
INVENTOR(S) : Christoph Johann Schmitz It is certified that error appears in the above-identified patent and that said Letters Patent is hereby corrected as shown below:

Replace drawing Figure 1, with the attached Figure 1.

Column 6,
Line 2, after "cuffs", delete ";" and insert -- , --.
Line 3, after the second occurrence of "of", insert -- the --.
Line 6, prior to "lifted", delete "directly".

Signed and Sealed this

Seventh Day of March, 2006

JON W. DUDAS
*Director of the United States Patent and Trademark Office*